(12) United States Patent
Sapian (10) Patent No.: US 7,938,645 B2
(45) Date of Patent: May 10, 2011

(54) DENTAL SYSTEM FOR ROOT AND ROOT TIP EXTRACTION

(76) Inventor: Schubert L. Sapian, Fort Worth, TX (US)

( * ) Notice: Subject to any disclaimer, the term of this patent is extended or adjusted under 35 U.S.C. 154(b) by 0 days.

(21) Appl. No.: 11/378,856

(22) Filed: Mar. 16, 2006

(65) Prior Publication Data

US 2007/0218423 A1 Sep. 20, 2007

(51) Int. Cl.
*A61C 3/00* (2006.01)

(52) U.S. Cl. .................................................... 433/152

(58) Field of Classification Search .......... 433/152–154, 433/156–159, 161–162, 165, 75–76, 102, 433/224, 146–149, 141, 81; 606/104
See application file for complete search history.

(56) References Cited

U.S. PATENT DOCUMENTS

| | | | |
|---|---|---|---|
| 5,865 A | 10/1848 | Dubs | |
| 2,210,349 A * | 8/1940 | Van Beeck | 433/152 |
| 2,404,684 A * | 7/1946 | Barishman | 433/47 |
| 3,394,449 A * | 7/1968 | Black | 29/278 |
| 4,198,754 A * | 4/1980 | Lares et al. | 433/129 |
| 4,230,454 A * | 10/1980 | Lococo | 433/153 |
| 4,247,285 A * | 1/1981 | Roig-Greene | 433/141 |
| 4,443,196 A | 4/1984 | Rico | |
| 5,971,987 A * | 10/1999 | Huxel et al. | 606/916 |
| 6,019,602 A | 2/2000 | Fletcher et al. | |
| 6,575,747 B1 * | 6/2003 | Riitano et al. | 433/102 |
| 2004/0126741 A1 * | 7/2004 | Hornig et al. | 433/152 |
| 2004/0236343 A1 * | 11/2004 | Taylor et al. | 606/108 |
| 2006/0057536 A1 * | 3/2006 | Tamburrino et al. | 433/30 |
| 2006/0131906 A1 * | 6/2006 | Maurer et al. | 433/141 |

\* cited by examiner

*Primary Examiner* — Cris L Rodriguez
*Assistant Examiner* — Heidi M Eide
(74) *Attorney, Agent, or Firm* — Morland C. Fischer (57) ABSTRACT

A compact, easily transportable dental system to permit root and root tip extractions from human and animal patients including those who are unable to visit an oral surgeon or veterinarian at a traditional office. An extraction bur having a lifting ball is embedded within and stands upwardly from the root or root tip to be extracted. The extraction bur is detachably connected to and rotated into the root/tip by a bur implanting device. A bur ejector is slidable through the bur implanting device to cause the extraction bur to be released therefrom once the bur has been implanted in the patient's root/tip. A universal fulcrum tray covers the root/tip and surrounds the patient's adjacent teeth during the extraction process. The upstanding extraction bur and the lifting ball thereof project through one of a pair of slots formed in the universal fulcrum tray. An extracting instrument having a pivot surface rotates over the universal fulcrum tray to apply a lifting force to the lifting ball of the extraction bur to pull the bur upwardly and the root/tip outwardly from its root socket.

1 Claim, 9 Drawing Sheets

DENTAL SYSTEM FOR ROOT AND ROOT TIP EXTRACTION

BACKGROUND OF THE INVENTION

1. Field of the Invention

This invention relates to a compact, easily transportable dental system to permit root and root tip extractions from dental patients, including those who are unable to visit a dentist or an oral surgeon at a traditional dental office.

2. Background Art

Because of gross decay and/or trauma, individuals are known to occasionally break a tooth. In addition, a dentist may break a crown during an extraction process. In these cases, a remaining root or a root tip may lie at or below the gumline. Some patients have the means and ability to visit an oral surgeon at a conventional medical facility. Other patients may live in a rural or remote geographic area where large scale and complex dental equipment is not readily accessible or practical. Still other patients may be confined to bed and unable to travel to an oral surgeon. Therefore, not all patients in need of an oral surgeon are able to receive prompt attention should the root or root tip be in need of extraction to avoid infection, discomfort or the appearance created as a consequence of a broken tooth.

Animals, like humans, are also susceptible to broken teeth. In many cases, it is not possible to transport an animal to a veterinarian or a similar healthcare worker to receive oral surgery.

What is therefore needed is a system including compact, portable dental instruments which can be employed in a traditional dental office environment and which may be transported for use outside the traditional office for treating both human and animal patients who require the extraction of a root or a root tip remaining from a broken tooth.

SUMMARY OF THE INVENTION

In general terms, a dental system is disclosed including dental instruments that are compact, easy to transport and ideally suited for treating those patients who are able to visit a traditional dental office and those patients who are unable to travel to an office environment. The dental instruments herein disclosed have particular application for use in a process to extract a root or a root tip that remains in the jawbone of a human or animal patient following a broken tooth.

The dental instruments disclosed herein include an extraction bur that can be coupled to a latch head from a slow speed latch dental handpiece so as to be rotated and embedded within the root or root tip to be extracted from the mouth of the patient. A set of barb-like screw threads enable the extraction bur to be affixed to the root or root tip. Located above the screw threads is a lifting ball to be captured by an extracting instrument to receive a vertical lifting or pulling force by which the root/tip can be extracted from its root socket. In the case of a curved root tip, the extraction bur may be flexible. A hollow guide sleeve is initially inserted into the root socket to guide the flexible bur towards and into alignment with the root tip to be extracted.

The extracting instrument to apply the vertical lifting or pulling force to the lifting ball of the extraction bur includes a handle at one end to permit the extraction instrument to be manipulated relative to the bur. Located at the opposite end is an extracting head having a pair of spaced prongs. The pair of prongs have first and second axially aligned sockets formed therebetween and sized to receive and support the lifting ball of the extraction bur. The extracting head is bent so as to have a curved configuration and establish a pivot surface at the bottom thereof around which the head can rotate during the extraction process.

A universal fulcrum tray includes an occlusal channel that is sized to surround the root or root tip to be extracted. An elastomer pad is bonded inside the occlusal channel to provide a cushion surface to avoid damage to the patient's teeth adjacent the root or tip to be removed during the extraction process. A swivel handle attached to the occlusal channel allows the fulcrum tray to be handled and positioned relative to the patient's teeth. Located at opposite ends of the occlusal channel are a pair of slots that are sized to receive therethrough the lifting ball of the extraction bur. Depending upon the alignment of the root or root tip in its root socket, the extraction bur will project upwardly therefrom and through one of the slots in the occlusal channel to enable access to the lifting ball of the bur.

To accomplish the extraction process, the extraction bur is rotated (by means of the slow speed latch handpiece) into and through a pilot hole formed in the patient's root or root tip to be extracted. Next, the universal fulcrum is positioned by means of its swivel handle over the root/tip so that the extraction bur and the lifting ball thereof project upwardly from the root/tip and through one of the slots formed in the occlusal channel of the fulcrum tray. The extracting instrument is then moved into sliding engagement with the upstanding extraction bur such that the lifting ball thereof is seated within one of the sockets formed between the prongs of the extracting head of the extracting instrument. The extracting instruments is rotated at its handle to cause the extracting head to rotate at its pivot surface and thereby apply a vertical lifting or pulling force against the lifting ball of the extraction bur. The root/tip affixed to the extraction bur receives a corresponding vertical extraction force by which to urge the root/tip upwardly relative to the patient's gumline and outwardly of the root socket in the patient's mouth.

A manually operated bur implanting device is provided in substitution of the slow speed latch handpiece to apply a rotational force to and thereby affix the extraction bur to the patient's root or root tip to be extracted so that the bur stands upwardly therefrom. The bur is releasably retained by a set of splines from a collet at one end of the bur implanting device. At the opposite end of the bur implanting device is a hollow handle within which a bur ejector is slidably received. The bur ejector has a bur releasing plunger at one end to which a pushing force is applied to cause the bur ejector to slide through the hollow handle. A plunger rod is located at the opposite end of the bur ejector for engaging the extraction bur and applying an ejection force thereto for causing the bur to be released by the splines of the collet and ejected from the bur implanting device in response to the pushing force applied to the bur releasing plunger thereof.

DESCRIPTION OF THE PREFERRED EMBODIMENT

Figure 1:
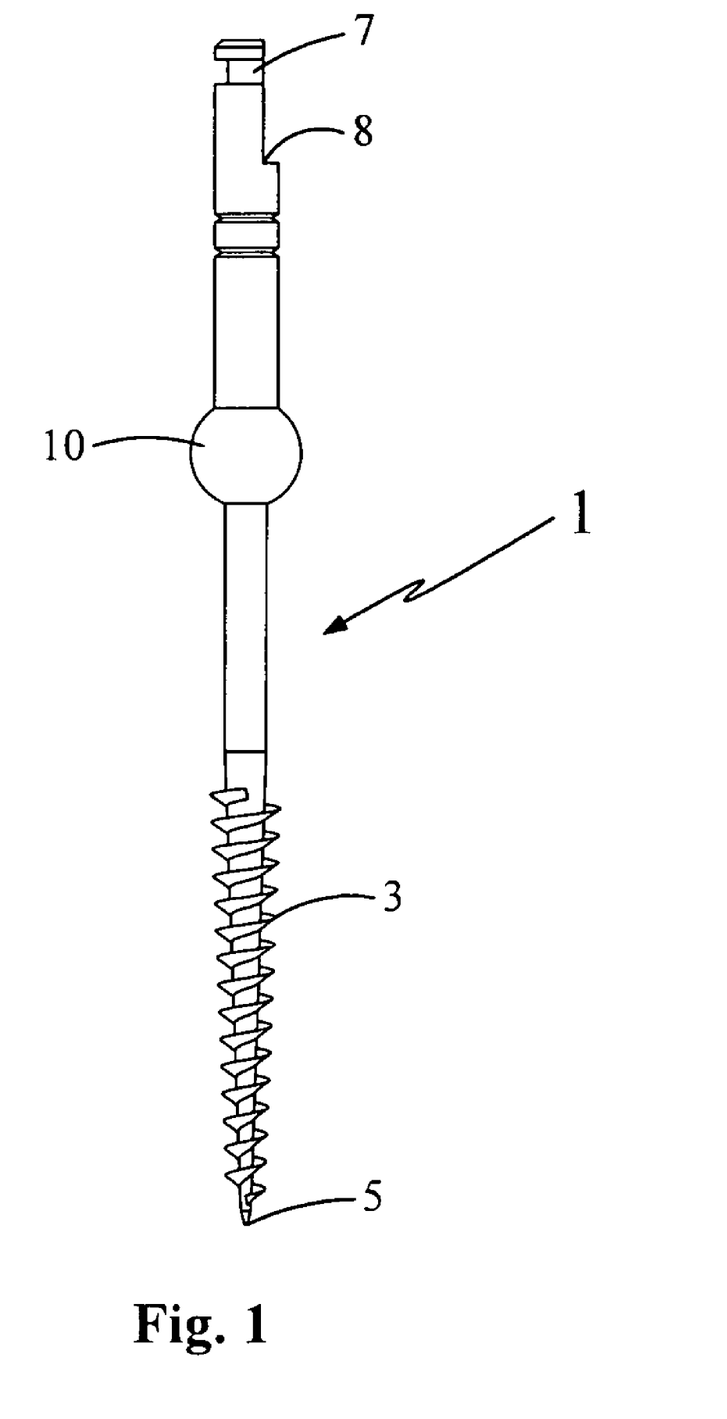
FIG. 1 shows an extraction bur as a part of a dental system for root and root tip extraction according to a preferred embodiment of the present invention.

FIG. 1 of the drawings shows an extraction bur 1 according to a preferred embodiment of this invention which, as will soon be described, is capable of removing a root or a root tip of a broken tooth which lies within the jawbone at or below the patient's gumline. The extraction bur 1 is adapted to be coupled to a latch head (designated 50 in FIG. 9) of a conventional slow speed latch dental handpiece by which the extraction bur can be rotated and embedded within the root or root tip to be extracted from the mouth of the patient. The extraction bur 1 is preferably manufactured from stainless steel or medical grade steel. However, bur 1 may also be manufactured from spring steel or a nickel/titanium alloy so as to have a flexible characteristic for a purpose to be described when referring to FIGS. 20-23.

Located at one end of the extraction bur 1 is a set of barb-like screw threads 3 which terminate at a pointed tip 5 to bore into the patient's root or root tip as the bur is rotated at slow speed by the dental handpiece. The screw threads 3 have sharp edges to catch onto the root or root tip to facilitate the extraction process. Located at the opposite end of the extraction bur 1 is a latch head 7 and a slot 8 by which the bur can be releasably coupled to the dental handpiece.

As an important feature, the extraction bur includes a lifting ball 10 located above the screw threads 3. For most extraction applications, the distance from the lifting ball 10 to the tip 5 of bur 1 is between 25-35 mm. The ball 10 is sized (with a diameter of about 4 mm) to be captured by an extracting instrument (designated 12 in FIGS. 2 and 3) so as to receive a vertical lifting or pulling force by which the bur 1 and the root or root tip of the tooth into which the bur has been embedded can be simultaneously uplifted.

Figures 2, 3, 4:
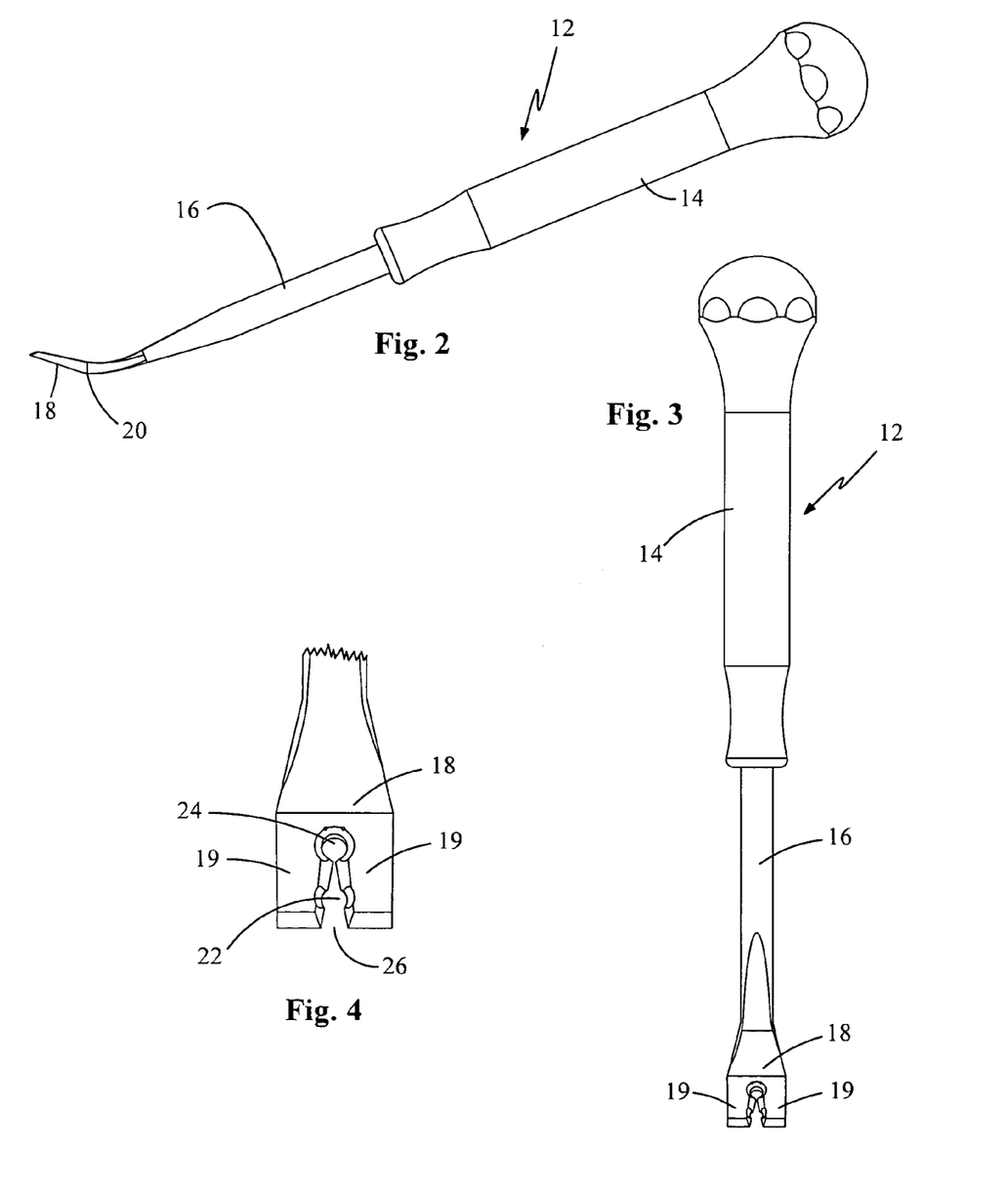
FIG. 2 is a side view of an extracting instrument as another part of the dental system for root and root tip extraction.
FIG. 3 is a top view of the extracting instrument shown in FIG. 2.
FIG. 4 is an enlarged view of the extracting head of the extracting instrument shown in FIGS. 2 and 3.

To this end, FIGS. 2-4 of the drawings illustrate an extracting instrument 12 by which to apply a vertical lifting or pulling force to the lifting ball 10 of the extraction bur 1 of FIG. 1 to cause the bur and the root or root tip to which the bur is attached to be extracted. The extracting instrument 12 includes a handle 14 at which the extracting instrument is grasped and manipulated during the root or root tip extraction process. An extracting bar 16 is surrounded at one end thereof by the handle 14. Located at the opposite end of the extracting bar 16 is an extracting head 18 having a pair of prongs 19 that are spaced from one another. The extracting bar 16 of the extracting instrument 12 is preferably manufactured from a metallic material such as, for example, aluminum, stainless steel or a titanium alloy.

As is best shown in FIG. 2, the extracting head 18 is bent (e.g., to make an angle of about 135 degrees) so as to have an arcuate configuration whereby a pivot surface 20 is formed at the underside thereof. As will be explained when referring hereinafter to FIGS. 9-12, the pivot surface 20 of extracting head 18 enables the extracting instrument 12 to function as a lever arm for applying a vertical extraction force against the root or root tip of the patient's tooth by way of the extraction bur 1 of FIG. 1.

More particularly, the pair of spaced prongs 19 at the extracting head 18 of extracting instrument 12 have first and second axially aligned sockets 22 and 24 (best shown in FIG. 4) formed therebetween. The forward-most socket 22 between the prongs 19 is wider than the rearward-most axially aligned socket 24. Both sockets 22 and 24 are sized to receive and support therewithin the lifting ball 10 from the extraction bur 1 of FIG. 1. That is, the extracting head 18 of extracting instrument 12 has an entrance opening 26 (of FIG. 4) through which the extraction bur 1 is positioned so that the lifting ball 10 thereof will be seated within one of the sockets 22 or 24 of extracting head 18.

In the case where the extraction bur 1 is relatively long, the lifting ball 10 will usually be seated within the forward-most socket 22 of extracting head 18. In the case where the extraction bur 1 is relatively short, the lifting ball 10 will usually be seated within the other (i.e., rearward-most) socket 24. With the lifting ball 10 of extraction bur 1 seated within one of the sockets 22 or 24, the extracting instrument 12 can be rotated around the pivot surface 20 of extracting head 18 to exert the lifting or pulling force against the lifting ball 10 that is necessary to cause an extraction of the root or the root tip from its root socket below the gumline.

Figure 5:
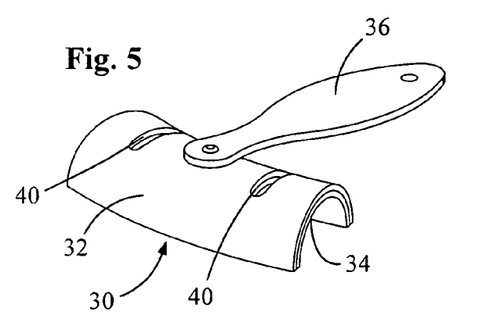
FIG. 5 is a perspective view of a universal fulcrum tray as still another part of the dental system for root and root tip extraction.
Figure 6:
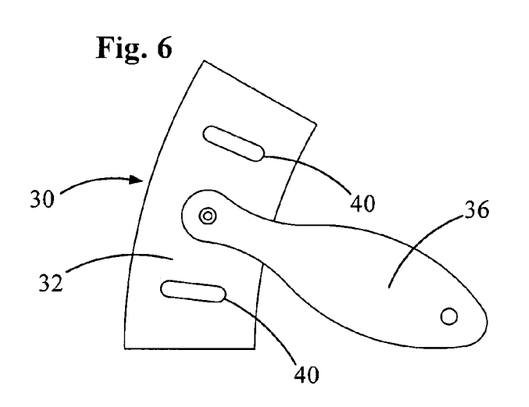
FIG. 6 is a top view of the universal fulcrum tray of FIG. 5.

Referring to FIGS. 4-6 of the drawings, a universal fulcrum tray 30 is shown to enable the extracting instrument 12 to be rotated around its pivot surface 20 to generate a sufficient lifting or pulling force against the lifting ball 10 of extraction bur 1 to extract the root or root tip. The universal fulcrum tray 30 is preferably manufactured from stainless steel or a high impact resistant plastic and is sized and shaped to surround a number of the patient's teeth which lie adjacent the root or root tip to be extracted. In the example of FIGS. 4-6, the fulcrum tray 30 is shown having a rounded occlusal channel 32. However, the fulcrum tray 30 can have other suitable shape so as to comfortably fit over and around the teeth of the patient. To this end, an autoclavable (e.g., silicone) elastomer pad 34 is bonded to the inside of the occlusal channel 32 to provide a cushion surface and thereby avoid damage to the patient's teeth during the root/tip extraction process.

Figure 7:
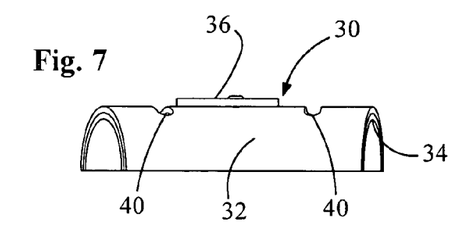
FIG. 7 is a rear view of the universal fulcrum tray of FIG. 5.

A swivel handle 36 is pivotally connected to the occlusal channel 32 of fulcrum tray 30 by means of a rivet, pin or similar fastener. The swivel handle 36 enables the occlusal channel 32 to be handled and positioned relative to the patient's teeth during the root/tip extraction process. The swivel handle 36 is rotatable so as not to interfere with the cooperation between the extracting instrument 12 (of FIGS.

2-4) and the extraction bur 1 (of FIG. 1) for generating the lifting or pulling force necessary to remove the root or root tip of the patient's tooth.

Located at opposite ends of the occlusal channel 32 of fulcrum tray 30 are a pair of elongated slots 40. The slots must be sufficiently wide to accommodate therethrough the lifting ball 10 of extraction bur 1 of FIG. 1. In the event that the root or root tip of the tooth to be extracted is aligned within its root socket at an angle, it may be necessary to manipulate the fulcrum tray 30 at the swivel handle 36 so that the extraction bur 1 (of FIG. 1) extends through one of the slots 40 at a corresponding angle.

Depending upon the alignment and location of the root or root tip surrounded by the occlusal channel 32, the extraction bur 1 will project upwardly and through one of the slots 40. The lifting ball 10 of the extraction bur 1 will lie above the occlusal channel 32 so as to be seated within one of the sockets 22 or 24 of the extracting head 18 of the extracting instrument 12 (of FIGS. 2-4). With the extracting head 18 of the extracting instrument 12 lying against the occlusal channel 32, the handle 14 of instrument 12 is manipulated to cause head 18 to rotate at its pivot surface 20 to apply a lifting or pulling force against the lifting ball 10 of bur 1 in a manner which will be detailed when referring hereinafter to FIGS. 9-12.

Figure 8:
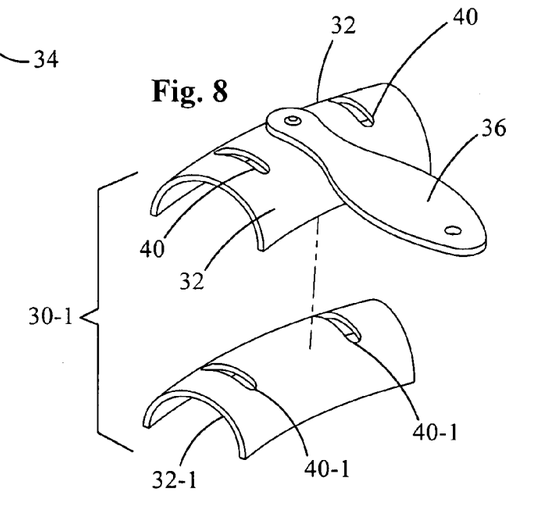
FIG. 8 is an exploded view of an alternate embodiment for a universal fulcrum tray.

An alternate embodiment for the universal fulcrum tray 30 of FIGS. 5-7 is shown in FIG. 8 of the drawings. Where it is necessary to extend the height of the occlusal channel 32 above the patient's root or root tip to be extracted, the elastomer pad (designated 34 in FIGS. 5-7) is replaced by an auxiliary occlusal channel 32-1. The auxiliary occlusal channel 32-1 is sized and shaped to conform to the size and shape of the occlusal channel 32. Moreover, the auxiliary occlusal channel 32-1 is provided with a pair of slots 40-1 that are aligned with the slots 40 formed in the occlusal channel 32.

The modified universal fulcrum tray 30-1 of FIG. 8 includes the auxiliary occlusal channel 32-1 positioned inside and below the occlusal channel 32 to form an interposer for effectively increasing the height of the fulcrum tray 30-1 and thereby enabling the extracting head 18 of the extracting instrument 12 to move into engagement with the lifting ball 10 of a tall standing extraction bur 1 that projects upwardly and outwardly through a pair of axially aligned slots 40 and 40-1 of the occlusal channels 32 and 32-1 of the modified fulcrum tray 30-1.

Figure 9:
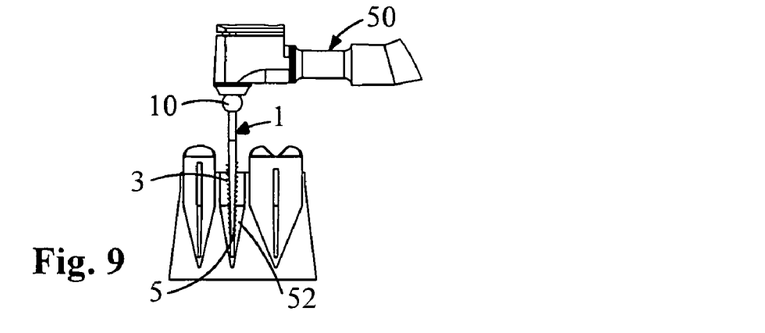
FIGS. 9-12 illustrate the steps by which the extraction bur, extracting instrument, and universal fulcrum tray from the dental system of FIGS. 1-7 cooperate with one another during an extraction process to remove a root or root tip from a root socket within the jawbone of a dental patient.

The method by which the extraction bur 1 (of FIG. 1), the extracting instrument 12 (of FIGS. 2-4) and the universal fulcrum tray 30 (of FIGS. 5-7) cooperate with one another during the extraction of the root or root tip of the patient's tooth from a root socket in the jawbone is now described while referring to FIGS. 9-12 of the drawings. In FIG. 9, the extraction bur 1 is shown coupled to a latch head 50 from a conventional compressed air or motor or manually driven slow speed dental handpiece. The handpiece applies a rotational force to the bur 1 by which the sharp screw threads 3 thereof bore into the root/tip 52 to be extracted from the patient's mouth. It may be preferable to initially drill a pilot hole into the root/tip so that the bur 1 may be more easily installed. Once the extraction bur 1 is affixed to the root/tip so as to stand upwardly therefrom, the latch head 50 of the handpiece is uncoupled from the bur 1.

Figure 10:
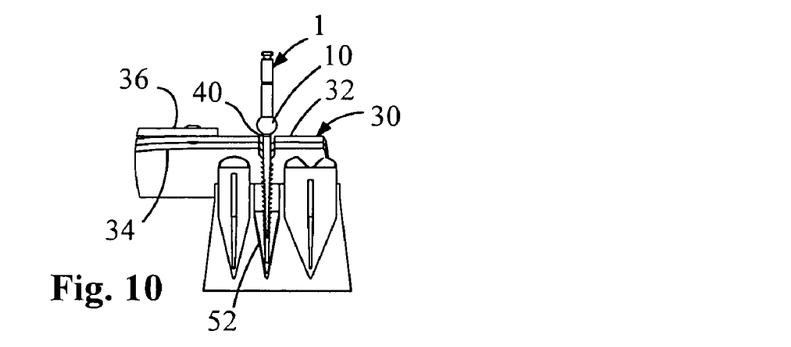

Next, in FIG. 10, the universal fulcrum 30 is positioned by its swivel handle 36 around a series of the patient's teeth within which lies the root or root tip 52 to be extracted. The occlusal channel 32 of fulcrum tray 30 is located above the root/tip 52 such that the elastomer pad 34 rests upon the adjacent teeth. The fulcrum tray 30 is manipulated at swivel handle 36 so that the extraction bur 1 projects upwardly from the root/tip 52 and through one of the slots 40 in the occlusal channel 32, whereby the lifting ball 10 of bur 1 is accessible above the slot 40.

Figure 11:
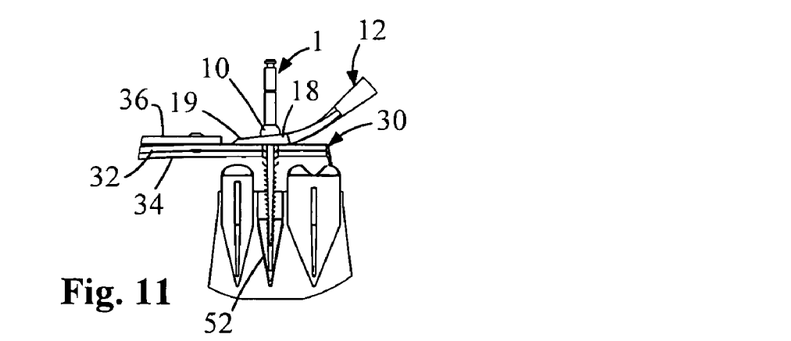

In FIG. 11, the extracting instrument 12 is then moved into sliding engagement with the extraction bur 1 that is embedded in and stands upwardly from the root/tip 52. In particular, the extracting head 18 of extracting instrument 12 slides along the top of the occlusal channel 32 of universal fulcrum tray 30 until the lifting ball 10 of bur 1 is disposed between the prongs 19 of extracting head 18. Depending upon the height of the lifting ball 10 above the fulcrum tray 30, ball 10 is seated within one of the sockets (designated 22 and 24 in FIG. 4) that are formed in the extracting head 18 of extracting instrument 12.

Figure 12:
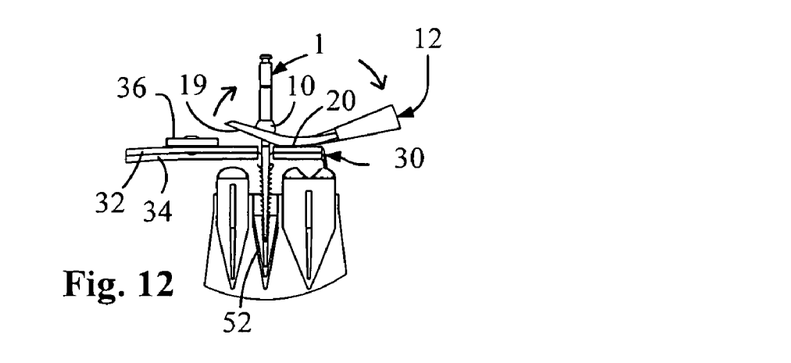

In FIG. 12, the extracting instrument 12 is manipulated (i.e., rotated) at its handle (designated 14 in FIGS. 2 and 3) to cause the extracting head 18 of instrument 12 to correspondingly rotate at its pivot surface 20 (in the direction of the reference arrows). The rotation of the head 18 is transmitted to the lifting ball 10 of extraction bur 1 as a vertical lifting or pulling force. The lifting or pulling force applied to the lifting ball 10 is transferred as a corresponding vertical extraction force to the root/tip 52 within which the bur 1 is embedded to cause the root/tip 52 to move upwardly relative to the patient's gumline. Accordingly, the extraction bur 1 will move upwardly through the slot 40 in the occlusal channel 32 until the root/tip 52 is extracted from its root socket. At this time, the extracting instrument 12, the universal fulcrum tray 30, and the extraction bur 1 attached to the root/tip 52 are all removed from the patient's mouth to complete the extraction process.

Figures 13, 13A:
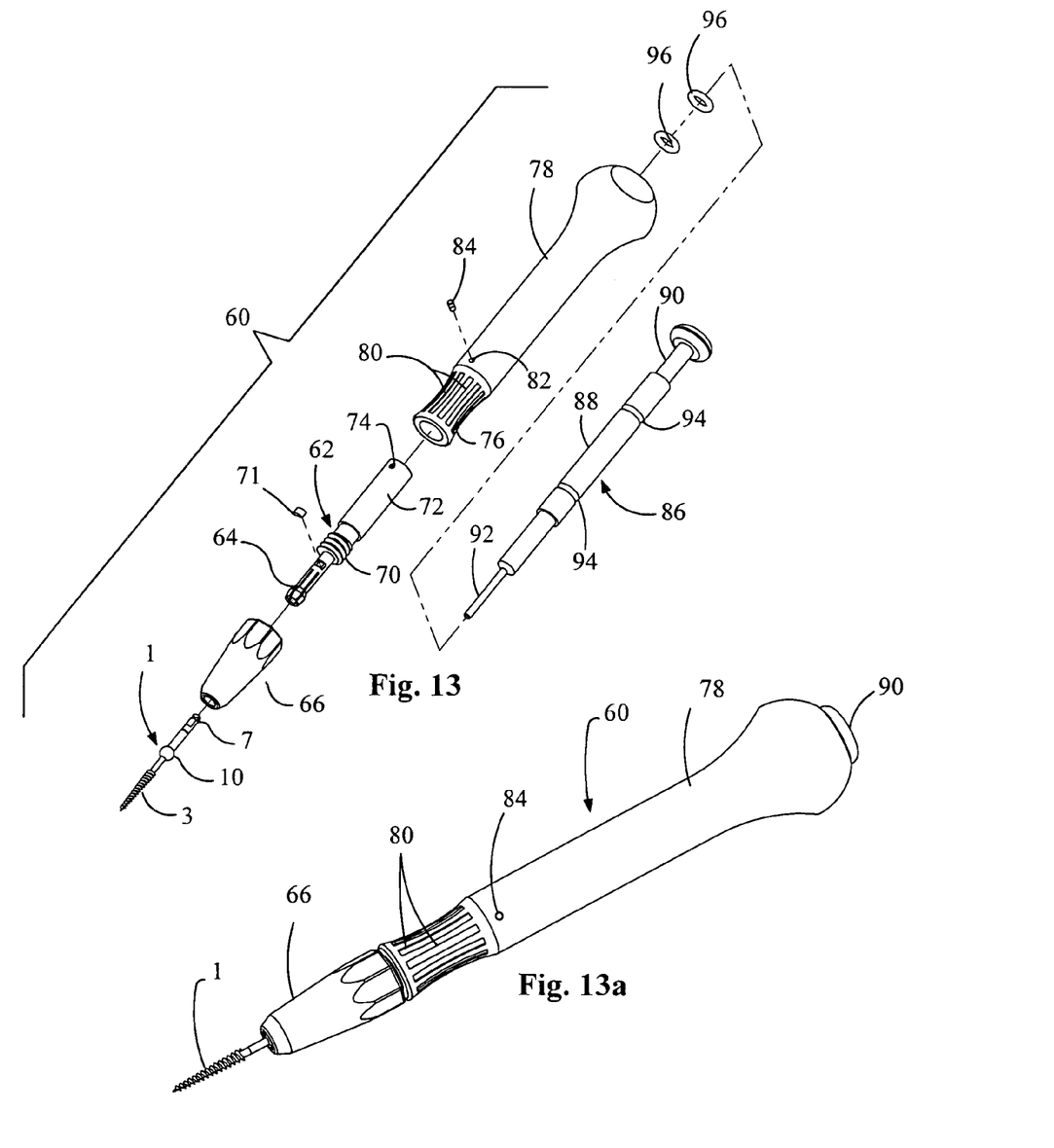
FIG. 13 is an exploded view of an extraction bur implanting device including an extraction bur ejector as yet another part of the dental system for root and root tip extraction.
FIG. 13a shows the bur implanting device of FIG. 13 in the assembled configuration.

The latch head 50 from the slow speed latch handpiece shown in FIG. 9 can be used to rotate the extraction bur 1 of FIG. 1 into engagement with a root or root tip at any location within the patient's mouth to be extracted according to the method described while referring to FIGS. 9-12. FIGS. 13 and 13*a* of the drawings show a manually powered anterior bur implanting device 60 which is ideally suited to rotate the bur 1 into an interior root or root tip at the front of the patient's mouth, especially in cases where a compressed air supply is not available. The bur implanting device 60 includes a collet 62 having a set of flexible splines 64 located at one end thereof. The splines 64 are arranged to collapse around and form a cavity within which to releasably receive the lifting ball 10 of bur 1.

Figure 14:
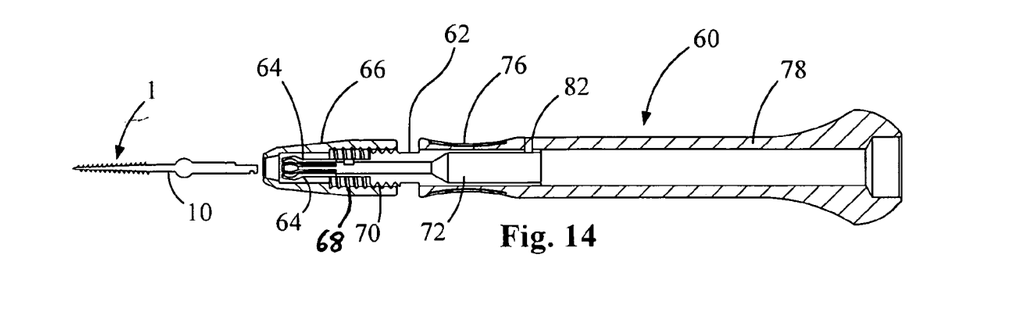
FIGS. 14 and 15 show the extraction bur detachably connected to the bur implanting device.
Figure 15:
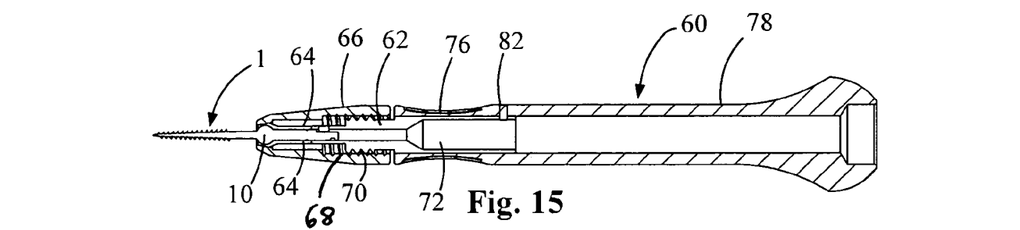

With the lifting ball 10 surrounded by the splines 64 of collet 62, a nut 66 is located in surrounding engagement with the splines. The nut 66 has a set of internal screw threads 68 (best shown in FIGS. 14 and 15) that are rotated into mating engagement with a corresponding set of screw threads 70 that run around the collet 62 behind the splines 64. As the nut 66 is tightened down against the screw threads 70, a compressive force is applied against the splines 64 so as to collapse the splines around the lifting ball 10 of the extraction bur 1, whereby the bur 1 is detachably connected to the anterior bur implanting device 60. A key 71 is located within a keyway (not shown) through collet 62 to engage the latch head 7 of extraction bur 1 to prevent a rotation of the bur relative to the collet.

The collet 62 also includes a hollow attachment rod 72 located opposite the set of splines 64. The attachment rod 72 of collet 62 has a screw threaded port 74 formed therein. The attachment rod 72 is sized to be slidably received within a hollow receiving barrel 76 of a hollow handle 78 of the bur implanting device 60. The receiving barrel 76 of handle 78 includes a plurality of parallel aligned and longitudinally extending slots 80 by which to provide the barrel 76 with a spring-like characteristic for surrounding and retaining therewithin the attachment rod 72 of collet 62. To prevent the collet 62 from rotating relative to the handle 78 and inadvertently sliding outwardly of the receiving barrel 76 of handle 78, an access port 82 is formed through the handle 78 behind the slots 80 thereof. In the assembled configuration of the anterior bur implanting device 60 shown in FIG. 13a, the screw threaded port 74 in the attachment rod 72 is axially aligned with the access port 82 formed in handle 78 so that a threaded insert 84 can be inserted therethrough.

As an important feature, FIG. 13 also shows a bur ejector 86 to be slidably received through the hollow handle 78 of the bur implanting device 60 by which to eject the bur 1 once the bur has been rotated and implanted within the root or root tip to be extracted. The bur ejector 86 includes an elongated body 88. A bur releasing plunger 90 extends from one end of the body 88 of bur ejector 86, and a plunger rod 92 extends from the opposite end. A pair of grooves 94 surround the body 88 of bur ejector 86 so as to receive respective O-rings 96 by which to frictionally engage the inside of the hollow handle 78 of bur implanting device 60 so as to retain the bur ejector 86 therewithin.

Figure 16:
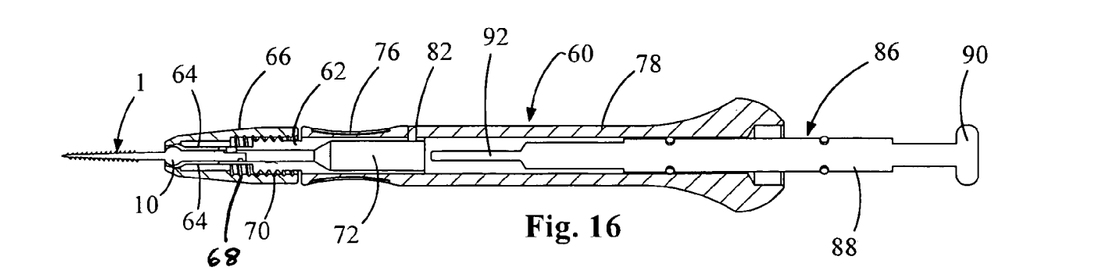
FIGS. 16-19 show the bur ejector generating an ejection force for ejecting the extraction bur from the bur implanting device.
Figure 17:
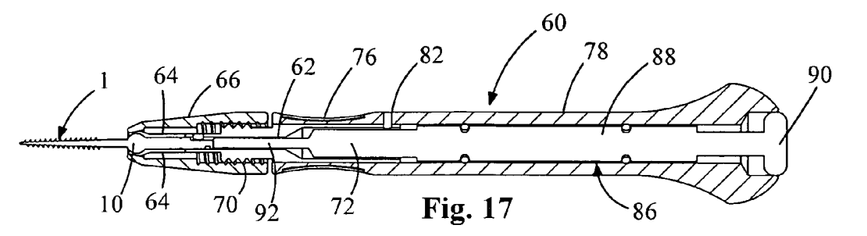

FIG. 16 shows the bur ejector 86 being loaded into the hollow handle 78 of the bur implanting device 60. In FIG. 17, the bur ejector 86 has been pushed through the hollow handle 78 and the hollow receiving barrel 76 thereof until the plunger rod 90 of bur ejector 86 moves through the hollow attachment rod 72 of collet 62 to lie in axial abutting alignment with the latch head 7 of extraction bur 1. With the bur ejector 86 loaded within and carried by the anterior bur implanting device 60 as shown in FIG. 17, a rotational force is manually applied to the handle 78. The rotational force is transferred to the extraction bur 1 so that the bur is correspondingly rotated and embedded within the root/tip to be extracted. If desirable, a pilot hole may first be made into the root/tip.

Figure 18:
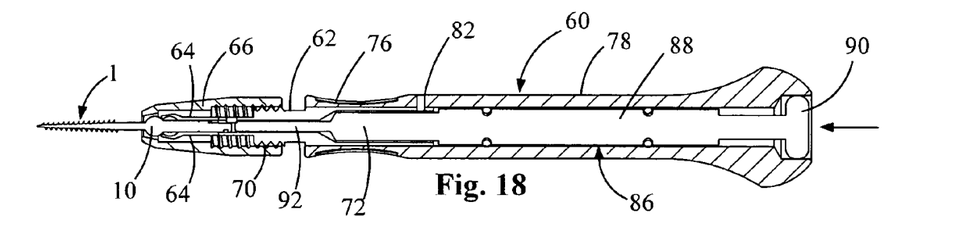

Once the extraction bur 1 is implanted in and standing upwardly from the root/tip, it is necessary to separate the bur 1 from the bur implanting device 60. To accomplish the foregoing, and referring now to FIG. 18, the threaded nut 66 is first unscrewed until the threads 70 of collet 62 are visible. A manual pushing force is then applied to the bur releasing plunger 90 of bur ejector 86 so as to drive the plunger rod 92 against the latch head 7 of extraction bur 1.

Figure 19:
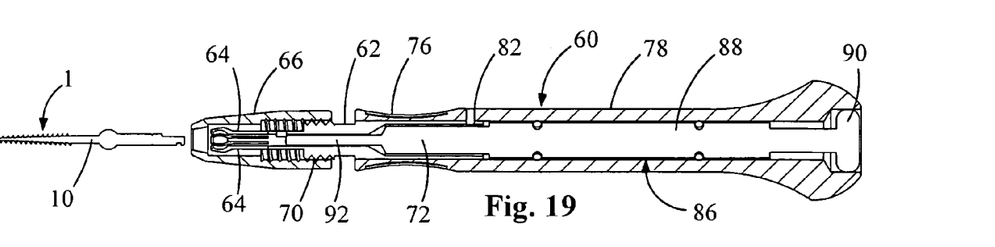

The bur ejector 86 will move axially through the interior of the bur implanting device 60, whereby to cause a corresponding axial displacement of the ejection bur 1. FIG. 19 of the drawings shows the bur 1 being pushed by the plunger rod 92 of bur ejector 86 so that the lifting ball 10 of bur 1 is released by the splines 64 of collet 62. Accordingly, the extraction bur 1 will now be ejected from the bur implanting device 60. At this time, the extracting bar 16 (of FIGS. 2-4) and the universal fulcrum tray 30 (of FIGS. 5-7) can be used in cooperation with the upstanding extraction bur 1 to complete the root/tip extraction process as has been earlier disclosed. A new bit inserted through the nut 66 and into the splines 64 of collet 62 will push the bur ejector 86 back to its loaded and ready position as shown in FIG. 17.

Figure 20:
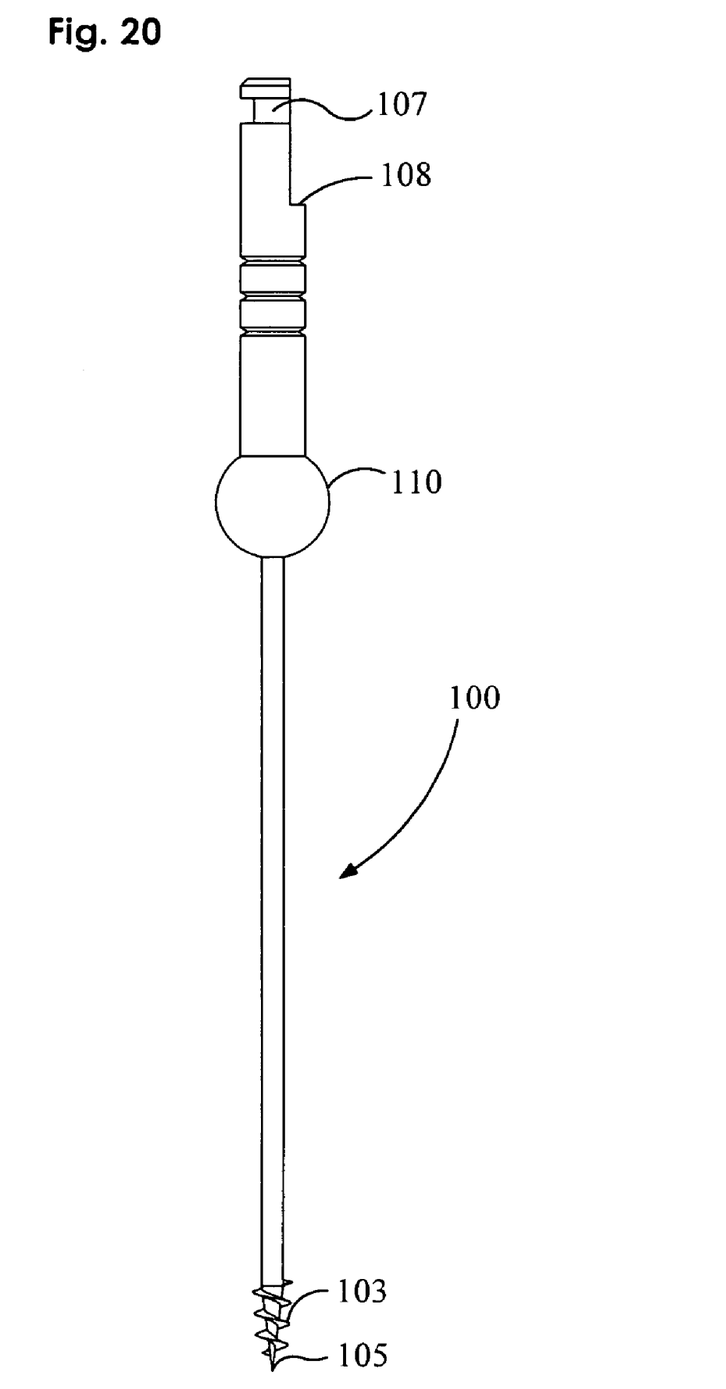
FIG. 20 shows a flexible extraction bur having particular application for extracting a curved root tip remnant.

As earlier disclosed, the extraction bur can be manufactured from a material (e.g., spring steel or a nickel/titanium alloy) so as to have a flexible characteristic in order to be particularly advantageous for extracting curved root tips from a root socket in the jawbone of a dental patient. FIG. 20 of the drawings shows such a flexible extraction bur 100 having a short set of screw threads 103 that terminates at a sharp pointed tip 105 to enable the bur 100 to penetrate the root tip in need of extraction. Like the extraction bur 1 of FIG. 1, the flexible extraction bur 100 of FIG. 20 includes a latch head 107, a slot 108, and a lifting ball 110.

A tooth (especially a molar) can have a curved root tip which is known to break during a tooth extraction process. Should this root tip be left behind in its root socket, the patient may encounter greater structural damage as a consequence of creating a gingival envelope flap and bone trauma which can occur following the extraction procedure and lead to delayed healing and possible infection. Therefore, it is desirable to remove the remnant root tip promptly so as to avoid post-surgical complications and the need for future implant placement at the extraction site.

Figure 21:
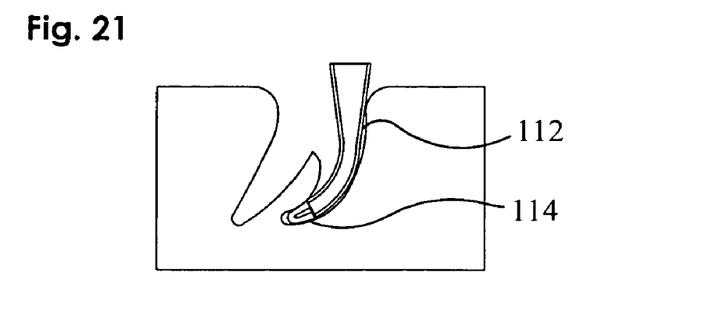
FIGS. 21-23 illustrate the steps by which the flexible extraction bur of FIG. 20 cooperates with the extracting instrument, the universal fulcrum tray, and a hollow, flexible guide sleeve during an extraction process to remove a curved root tip from a root socket within the jawbone of a dental patient.
Figure 22:
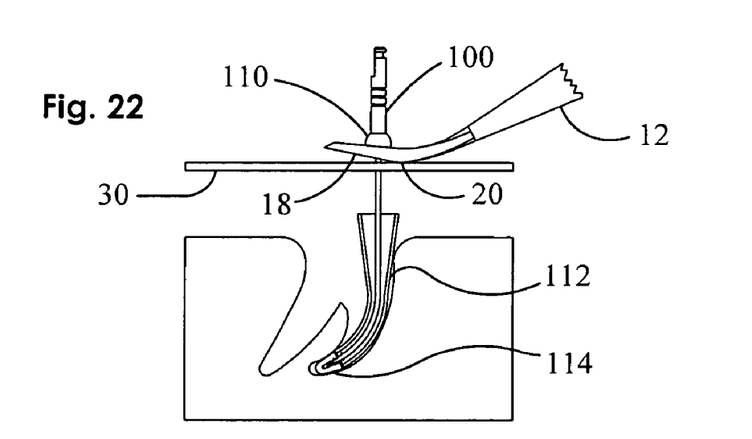
Figure 23:
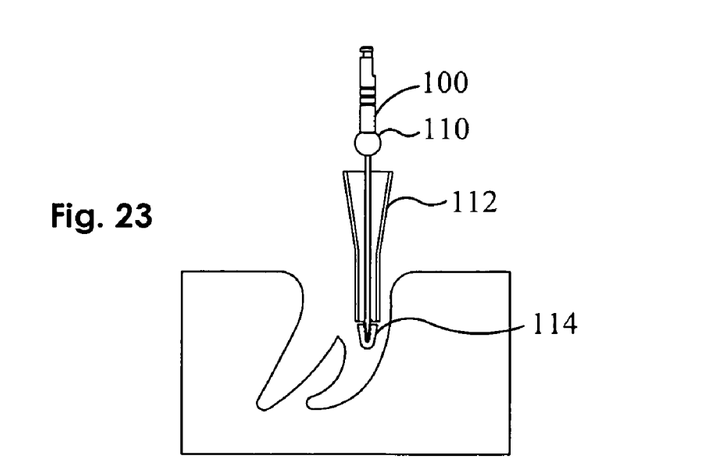

To accomplish the foregoing, and referring to FIGS. 21-23 of the drawings, a flexible, hollow guide sleeve 112 is sized to fit within the root socket within which a curved root tip 114 remains. The guide sleeve 112 is preferably tapered to match the usual taper of the root socket. FIG. 21 shows the hollow guide sleeve being inserted into the patient's root socket above the root tip 114 to be extracted. The sleeve 112 guides the pointed tip 105 of the flexible extraction bur 100 down the root socket and into alignment with the root tip 114. The anterior bur implanting device 60 of FIGS. 13 and 13a may be used to rotate the screw threads 103 of bur 1 at slow speed into mating engagement with the remaining root tip 114 to be extracted.

FIG. 22 shows the flexible extraction bur 100 being received through the flexible, hollow guide sleeve 112 and affixed to the root tip 114. The extracting instrument 12 and the universal fulcrum tray 30 may now be used in combination with the flexible extraction bur 100 in the manner that was previously disclosed while referring to FIGS. 10-12 to extract the root tip 114. Briefly, the extracting head 18 of extracting instrument 12 engages the lifting ball 110 of bur 100. As the pivot surface 20 of extracting instrument 12 rotates over the fulcrum tray 30, a pulling force is applied from the extracting head 18 to the lifting ball 10 of flexible extraction bur 100. A corresponding extraction force is applied from bur 100 to the root tip 114, whereby to remove the root tip from its root socket in the patient's jawbone.

FIG. 23 shows the remnant root tip 114 carried by the flexible extraction bur 100 being removed from the root socket along with the guide sleeve 112 at the conclusion of the extraction process.

The dental system and method herein disclosed for extracting a root or a root tip can be effectively practiced to efficiently treat a patient within a typical dental office or away from an office (e.g., such as in the field or at a geographically remote or rural area). Moreover, the system and method are applicable to treating both human and animal patients. The disclosed system is advantageously lightweight, compact and easy to transport by mobile healthcare workers.

The invention claimed is:

1. A dental system for extracting a tooth portion from a socket in the jawbone of a human or an animal patient, said dental system comprising:
   a flexible extraction bur having a sharp first end so as to be attached to and stand upwardly from the tooth portion to be extracted in response to a rotation of said extraction bur, said extraction bur also having a lifting element to which a lifting force is applied;
   an extracting instrument adapted to engage the lifting element of said extraction bur and apply said lifting force thereto such that a corresponding extraction force is applied from said extraction bur to the tooth portion to which said extraction bur is attached for causing said tooth portion to be extracted from its root socket in the mouth of the patient; and a hollow flexible sleeve sized to surround said flexible extraction bur and be received within the patient's socket, said flexible sleeve adapted to bend when the socket is curved for correspondingly bending and guiding said flexible extraction bur through the socket and into alignment with the tooth portion to be extracted.

* * * * *